(12) United States Patent
Sonoke et al.

(10) Patent No.: US 8,466,255 B2
(45) Date of Patent: Jun. 18, 2013

(54) POLYETHYLENE GLYCOL DERIVATIVE

(75) Inventors: Satoru Sonoke, Tsukuba (JP); Toshihiro Ueda, Tsukuba (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 622 days.

(21) Appl. No.: 12/525,570

(22) PCT Filed: Feb. 4, 2008

(86) PCT No.: PCT/JP2008/051719
§ 371 (c)(1),
(2), (4) Date: Aug. 3, 2009

(87) PCT Pub. No.: WO2008/096690
PCT Pub. Date: Aug. 14, 2008

(65) Prior Publication Data
US 2010/0074880 A1    Mar. 25, 2010

(30) Foreign Application Priority Data

Feb. 5, 2007 (JP) ................................. 2007-024992
Jul. 5, 2007 (JP) ................................. 2007-176827

(51) Int. Cl.
*C08G 65/04* (2006.01)

(52) U.S. Cl.
USPC ......... 528/421; 424/450; 424/486; 424/78.38

(58) Field of Classification Search
USPC ...................... 528/421; 424/78.38, 450, 486
See application file for complete search history.

(56) References Cited

U.S. PATENT DOCUMENTS

| 6,586,001 B1 | 7/2003 | Zalipsky |
| 2005/0175682 A1 | 8/2005 | Heyes et al. |
| 2006/0211642 A1 | 9/2006 | McSwiggen |
| 2007/0042979 A1* | 2/2007 | Yano et al. ...................... 514/44 |
| 2007/0244058 A1 | 10/2007 | Ohgi |

FOREIGN PATENT DOCUMENTS

| EP | 0685457 A1 | 12/1995 |
| EP | 1029544 A1 | 8/2000 |
| EP | 1064950 A1 | 1/2001 |
| EP | 1 783 137 | 5/2007 |
| EP | 2 119 738 | 11/2009 |
| JP | 2000281569 | 10/2000 |
| JP | 2003-505401 A | 2/2003 |
| JP | 2007-505954 A | 3/2007 |
| WO | WO-94/19314 | 9/1994 |
| WO | WO-9748712 | 12/1997 |
| WO | WO-99/20283 | 4/1999 |
| WO | WO-99/48531 | 9/1999 |
| WO | WO 2004/105774 * | 5/2004 |
| WO | WO 2004-078121 | 9/2004 |
| WO | WO 2005-000360 | 1/2005 |
| WO | WO 2005-026372 | 3/2005 |
| WO | WO-2005030835 | 4/2005 |
| WO | WO 2006-022325 | 3/2006 |

OTHER PUBLICATIONS

Translation of the International Preliminary Examination Report on Patentability (Chap I) issued Aug. 11, 2009 in International Application No. PCT/JP2008/051719.
Hirabayashi et al., "Inhibition of cancer cell growth by polyinosinic-polycytidylic acid/cationic liposome complex: A new biological activity", Cancer Research 59, 4325-4333 (Sep. 1, 1999).
Hirabayashi et al., Inhibition of Metastatic Carcinoma Cell Growth in Livers by Poly(I):Poly(C)/Cationic Liposome Complex (LIC), Oncology Research, vol. 11, pp. 497-504, 1999.
Extended European Search Report (EESR) dated Jul. 14, 2011 for EP 2 119 738, which is the EP counterpart to the instant application.

* cited by examiner

*Primary Examiner* — Robert Jones, Jr.
(74) *Attorney, Agent, or Firm* — McDermott Will & Emery LLP

(57) ABSTRACT

The present invention includes a novel polyethylene glycol derivative; a drug carrier comprising the derivative; and a pharmaceutical composition comprising the drug carrier having a pharmacologically active substance included therein. Specifically disclosed are: a polyethylene glycol derivative represented by the general formula (I); a drug carrier comprising the derivative and 2-O-(2-diethylaminoethyl)carbamoyl-1,3-O-dioleoyl-glycerol; and a pharmaceutical composition comprising the drug carrier and a pharmacologically active substance (preferably double-stranded RNA, double-stranded DNA or an oligonucleic acid), wherein R represents a saturated or unsaturated aliphatic hydrocarbon group having 10 to 30 carbon atoms or a saturated or unsaturated fatty acid residue having 10 to 30 carbon atoms; and n represents an integer of 30 to 150.

9 Claims, 5 Drawing Sheets

POLYETHYLENE GLYCOL DERIVATIVE

This application is a U.S. national phase application under 35 U.S.C. §371 of International Patent Application No. PCT/JP2008/051719 filed Apr. 2, 2008, which claims the benefit of priority to Japanese Patent Application No. 2007-024992 filed Feb. 5, 2007 and to Japanese Patent Application No. 2007-176827 filed Jul. 5, 2007, the disclosures of all of which are hereby incorporated by reference in their entireties. The International Application was published in Japanese on Aug. 14, 2008 as WO 2008/096690.

FIELD OF THE INVENTION

The present invention relates to a novel polyethylene glycol derivative.

BACKGROUND OF THE INVENTION

Attention has been focused recently on nucleic acid medicines such as synthetic double-stranded RNA such as poly(I)●poly(C), short interfering RNA (siRNA) utilizing RNA interference (RNAi), microRNA (miRNA), short hairpin RNA (shRNA), antisense DNA and antisense RNA, which have been actively investigated. Among the nucleic acid medicines, nucleic acid medicines like siRNA are hardly delivered to a tissue with a lesion even when the medicines are administered independently and systemically from for example a vein. Therefore, it is needed to administer such nucleic acid medicines after given treatments such as allowing an appropriate carrier to include the nucleic acid medicines for administration or administering the nucleic acid medicines topically to a tissue with a lesion.

The carrier for delivering such nucleic acid medicines to a tissue with a lesion includes for example cationic liposomes such as LIPOFECTIN (under trade mark), LIPOFECTOAMINE 2000 (under trade mark) and OLIGOFECTOAMINE (under trade mark) and cationic liposomes (hereinafter, referred to as "Compound A liposome") containing 2-O-(2-diethylaminoethyl)carbamoyl-1,3-O-dioleoylglycerol (hereinafter, referred to as "Compound A") and a phospholipid as the essential components (see for example WO 94/19314). Since these cationic liposomes likely accumulate readily in liver and spleen when administered systemically from for example a vein, it is expected to apply the cationic liposomes as therapeutic agents of liver cancer and hepatitis by allowing the cationic liposomes to include nucleic acid medicines. It is actually reported that complexes of Compound A liposome with for example synthetic double-stranded RNA such as poly(I)●poly (C) are effective for the treatment of liver cancer and hepatitis (see for example WO 99/20283, WO 99/48531, Kazuko Hirabayashi, et al., Cancer Research, 1999, Vol. 59, p. 4325-4333, and Kazuko Hirabayashi, et al., Oncology Research, 1999, Vol. 11, p. 497-504).

DETAILED DESCRIPTION

Problems that the Invention is to Solve

It is an object of the present invention to mainly provide a novel polyethylene glycol derivative, a drug carrier containing such a polyethylene glycol derivative and Compound A as the essential components, and a pharmaceutical composition containing the drug carrier including a pharmaceutical agent therein.

Means for Solving the Problems

The present invention is further described below in Examples 1 to 3. Thus, the inventors achieved the present inventions.

Exemplary Embodiment 1

A polyethylene glycol derivative represented by the following general formula (I) (hereinafter, referred to as "the derivative of the present invention"):

[Chemical scheme 1]

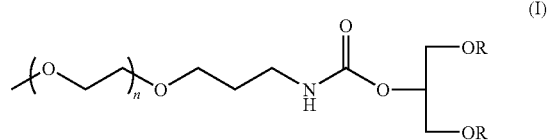

In the formula (I), R represents a saturated or unsaturated aliphatic hydrocarbon group with 10 to 30 carbon atoms or a saturated or unsaturated fatty acid residue with 10 to 30 carbon atoms; and n represents an integer of 30 to 150.

Exemplary Embodiment 2

A drug carrier containing the polyethylene glycol derivative described in Exemplary Embodiment 1 and Compound A as the essential components (hereinafter, referred to as "the carrier of the present invention"):

Exemplary Embodiment 3

A pharmaceutical composition containing the drug carrier described in Exemplary Embodiment 2 including a pharmaceutical agent therein (hereinafter, referred to as "the composition of the present invention").

The saturated aliphatic hydrocarbon group with 10 to 30 carbon atoms of R includes for example capryl, lauryl, myristyl, palmityl, and stearyl. Among the groups, a saturated aliphatic hydrocarbon group with 10 to 20 carbon atoms is preferable and particularly, stearyl is more preferable. Additionally, the unsaturated aliphatic carbon group with 10 to 30 carbon atoms includes for example oleyl, linoleyl, and arachidonyl. Among the groups, an unsaturated aliphatic hydrocarbon group with 10 to 20 carbon atoms is preferable and particularly, oleyl is more preferable.

The saturated fatty acid residue with 10 to 30 carbon atoms of R includes for example caproyl, lauroyl, myristoyl, palmitoyl, stearoyl, arachidoyl, behenoyl, lignoceroyl, cerotoyl, montanoyl, and melisoyl. Among the residues, a saturated fatty acid residue with 10 to 20 carbon atoms is preferable and particularly, stearoyl is more preferable. The unsaturated fatty acid residue with to 30 carbon atoms includes for example oleoyl, linoleoyl, arachidonoyl, and nervonoyl. Among the residues, an unsaturated fatty acid residue with 10 to 20 carbon atoms is preferable and particularly, oleoyl is more preferable.

As used herein, "n" is an integer within a range of 30 to 150. Preferably, "n" is an integer within a range of 30 to 100, and is more preferably an integer within a range of 30 to 50.

The derivative of the present invention preferably includes for example (1) 2-O-(methoxypolyethylene glycol propyl)carbamoyl-1,3-O-dioleoylglycerol or
(2) 2-O-(methoxypolyethylene glycol propyl)carbamoyl-1,3-O-distearoylglycerol.

I. PROCESS OF PRODUCING THE DERIVATIVE OF THE PRESENT INVENTION

Figure 1:
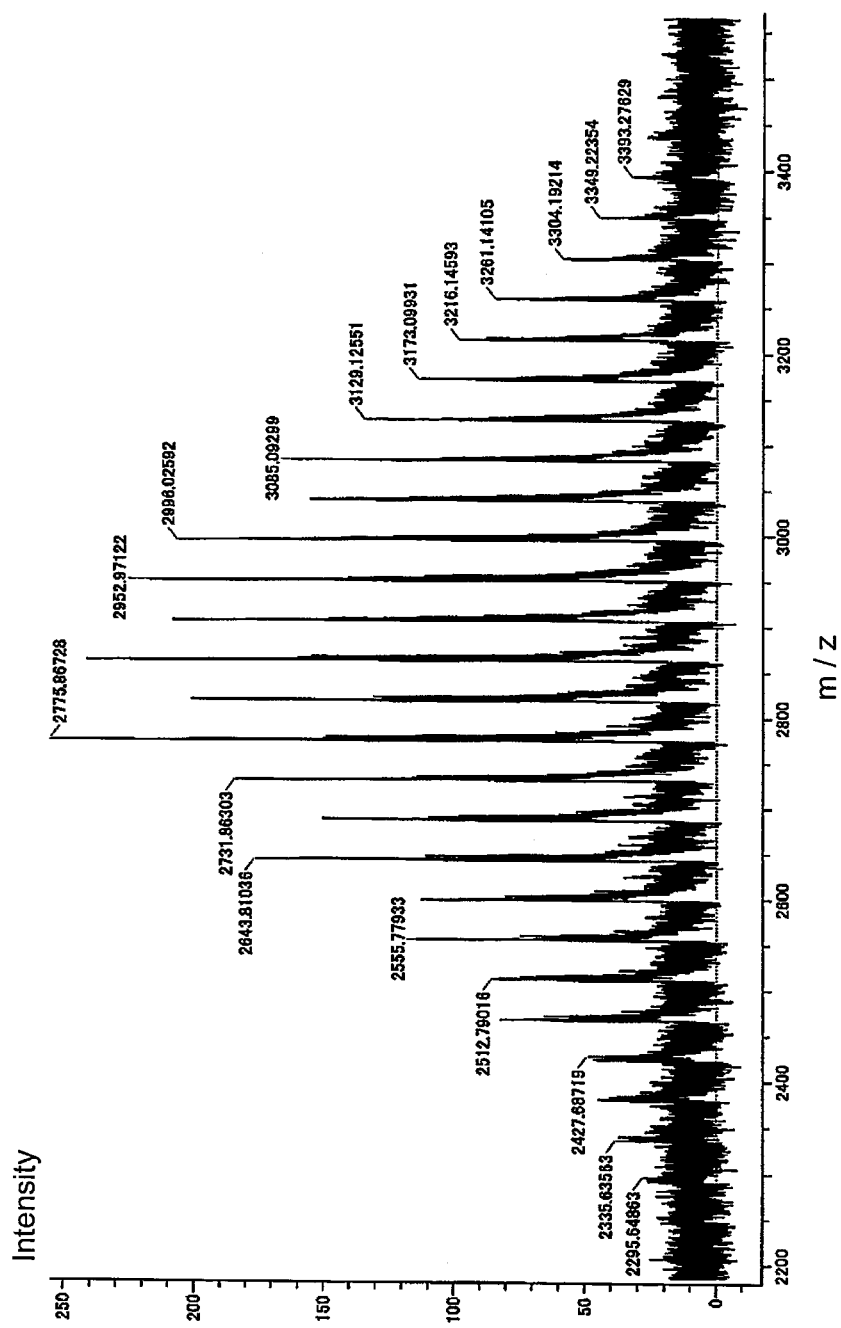
FIG. 1 shows the mass spectrum of the derivative of the present invention synthetically prepared in Example 1.

The derivative of the present invention (I) can be produced by dissolving an alcohol represented by the following general formula (1) in an appropriate solvent, for treatment with an appropriate acylating agent, and allowing the treated product to react with an amine derivative represented by the following general formula (2). Any solvent may be used with no specific limitation, as long as the solvent does not participate in the reaction. The solvent includes for example organic amines (for example, pyridine, picoline and collidine), dimethylformamide, or mixture solvents thereof. The acylating agent includes for example N,N'-carbonyldiimidazol and phenyl chlorocarbonate. The appropriate reaction temperature is within a range of 0 to 100° C. Further, the reaction time varies depending on the types of the raw materials used, and the reaction temperature. However, the reaction time is generally within a range of one to 30 hours.

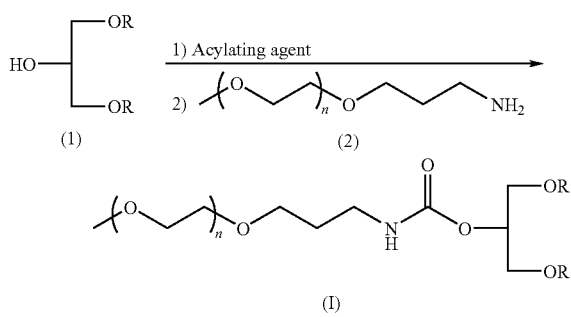

(in the formula, "R" and "n" have the same meanings as described above.)

Using the known dihydroxyacetone dimer (3), the alcohol (1) can be produced according to the method described in the reference (The Journal of Organic Chemistry, 1970, Vol. 35, p. 2082-2083), which is represented for example by the following steps. The condensation agent includes for example N,N'-dicyclohexylcarbodiimide, 1-ethyl-3-(3-dimethylaminopropyl)carbodiimide, and 1-hydroxybenzotriazole. The reducing agent includes for example sodium borohydride.

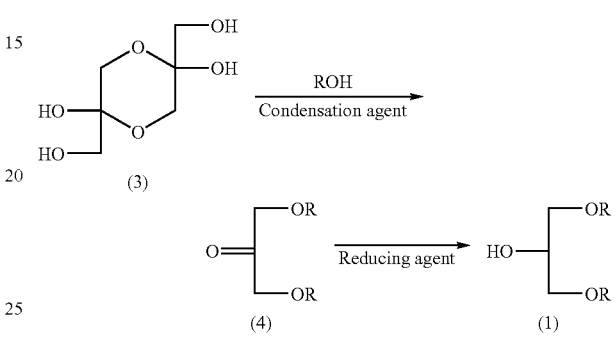

(in the formula, R has the same meaning as described above.)

II. THE CARRIER OF THE PRESENT INVENTION

The carrier of the present invention contains the derivative of the present invention and Compound A as the essential components. Specifically, the carrier of the present invention may take forms of for example liposome and fat emulsions.

Compound A can be prepared synthetically by the method described in WO 94/19314.

The ratio of the derivative of the present invention and Compound A in blend in the carrier of the present invention is appropriately within a range of 0.005 to 10 parts by weight, and is preferably within a range of 0.01 to 5 parts by weight and more preferably within a range of 0.05 to 3 parts by weight of the derivative of the present invention per one part by weight of Compound A.

In addition to the essential components, namely the derivative of the present invention and Compound A, a phospholipid can be added to the carrier of the present invention. Preferably, such phospholipid is added. Such phospholipid is not particularly limited insofar as it is a pharmaceutically acceptable lipid, and include, for example, phosphatidylcholine, phosphatidylethanolamine, phosphatidylinositol, phosphatidylserine, sphingomyelin, lecithin, dipalmitoylphosphatidylcholine, distearoylphosphatidylcholine, and dipalmitoylphosphatidylglycerol. These may be used singly or in combination of two or more thereof. Among such phospholipids, particularly, egg yolk phosphatidylcholine, egg yolk lecithin, and soybean lecithin are preferable.

In case of adding such phospholipid, the formulating ratio of the derivative of the present invention and such phospholipid in the carrier of the present invention is appropriately within a range of 0.005 to 100 parts by weight, and is preferably within a range of 0.01 to 50 parts by weight and more preferably within a range of 0.05 to 10 parts by weight of the derivative of the present invention per one part of the phospholipid. The sum of the derivative of the present invention and the phospholipid is appropriately within a range of 0.01 to 10 parts by weight, and is preferably within a range of 0.05 to 5 parts by weight and more preferably within a range of 0.5 to 3 parts by weight per one part by weight of Compound A.

In addition to the essential components, the derivative of the present invention and Compound A, cholesterol may be added to the carrier of the present invention. In case of adding cholesterol, the formulating ratio of the derivative of the present invention and cholesterol in the carrier of the present invention is appropriately within a range of 0.005 to 100 parts by weight, and is preferably within a range of 0.01 to 50 parts by weight and more preferably within a range of 0.05 to 10 parts by weight of the derivative of the present invention per one part by weight of cholesterol. The sum of the derivative of the present invention and cholesterol is appropriately within a range of 0.01 to 10 parts by weight, and is preferably within a range of 0.05 to 5 parts by weight and more preferably within a range of 0.1 to 3 parts by weight per one part by weight of the Compound A.

A dispersion of the carrier of the present invention may be prepared by mixing together (1) the derivative of the present invention and Compound A, (2) the derivative of the present invention, Compound A and the phospholipid, or (3) the derivative of the present invention, Compound A and cholesterol and dispersing the resulting mixture in an aqueous solution by conventional methods. For dispersion, apparatuses such as ultrasonic dispersion apparatus and emulsification dispersion apparatus may appropriately be used.

III. THE COMPOSITION OF THE PRESENT INVENTION

"The pharmaceutical agent" for use in the composition of the present invention includes for example water-soluble anionic compounds, anti-cancer agents, anti-viral agents and antibiotics. Specifically, the pharmaceutical agent includes for example nucleic acid compounds such as single-stranded or double-stranded RNA, single-stranded or double-stranded DNA or oligonucleic acids, acidic sugars such as heparan sulfate and dextran sulfate, cytokines, second messengers such as cyclic AMP, ATP and IP3, penicillins and cephalosporins, vitamins such as vitamin C and retinols, and other existing pharmaceutical agents with acidic groups, such as interferons (α, β, γ), interleukins (IL-1, IL-2), colony-stimulating factor (CSF), tumor necrosis factors (TNF), levamisol, pestatin, retinoic acid, 5-fluorouracil (5-FU), cytosine arabinoside (Ara-C), adenine arabinoside (Ara-A), cisplatinum (CDDP), cyclophosphamide, and azidothymidine (AZT).

The synthetic double-stranded RNA includes for example those described below.
1. Homopolymer.homopolymer complexes
Polyinosinic acid.polycytidylic acid,
Polyinosinic acid.poly(5-bromocytidylic acid),
Polyinosinic acid.poly(2-thiocytidylic acid),
Poly(7-deazainosinic acid).polycytidylic acid,
Poly(7-deazainosinic acid).poly(5-bromocytidylic acid),
Poly(2'-azidoinosinic acid).polycytidylic acid,
Polyinosinic acid.poly(cytidine-5'-thiophosphate).
2. Homopolymer.copolymer complex
Polyinosinic acid.poly(cytidylic acid, uridylic acid)
Polyinosinic acid.poly(cytidylic acid, 4-thiouridylic acid)
3. Complex of synthetic nucleic acid and polycation
Polyinosinic acid.polycytidylic acid.poly-L-lysine
4. Others
Polyinosinic acid.poly(1-vinylcytidylic acid).

The oligonucleic acid includes for example RNA, DNA and compounds thereof, which have nucleotides within a range of 10 to 200, preferably 15 to 150, more preferably to 100 within the molecule. The oligonucleic acid includes for example siRNA, miRNA, shRNA, non-coding RNA, anti-sense DNA, antisense RNA, DNA enzyme, ribozyme and aptamer.

The oligonucleic acid is not limited to naturally occurring types. So as to enhance the biological stability such as nuclease resistance, at least a part of sugars or phosphate backbones composing the nucleotides may be modified. Such modification includes for example ribose modification at the 2'-position, ribose modification at other positions, and modifications of the phosphate backbones. For example, such ribose modification at the 2'-position includes for example modifications by substituting the hydroxyl group at the 2'-position in ribose with H, $OR^1$, $R^1$, $R^2OR^1$, SH, $SR^1$, $NH_2$, $NHR^1$, $N(R^1)_2$, $N_3$, CN, F, Cl, Br and I. Herein, $R^1$ represents alkyl or aryl. $R^2$ represents alkylene.

The alkyl of $R^1$ is not particularly limited to the form of straight or branched chain, and includes for example alkyls with one to 6 carbon atoms. Specifically, the alkyl includes for example, methyl, ethyl, n-propyl, isopropyl, n-butyl, isobutyl, sec-butyl, tert-butyl, n-pentyl, isopentyl, neopentyl, tert-pentyl, n-hexyl, and isohexyl. The alkyl may satisfactorily be substituted with substituents including for example halogen, alkyl, alkoxy, cyano and nitro, and the substituents may satisfactorily be one to three in number. Such halogen includes fluorine, chlorine, bromine and iodine. Such alkyl include the same groups described above. The alkoxy is not particularly limited to the form of straight or branched chain, and includes for example alkoxy with one to 6 carbon atoms. Specifically, the alkoxy includes for example methoxy, ethoxy, n-propoxy, isopropoxy, n-butoxy, isobutoxy, sec-butoxy, tert-butoxy, n-pentyloxy, isopentyloxy, n-hexyloxy, and isohexyloxy. Among them, alkoxy with one to 3 carbon atoms is particularly preferable.

The aryl of $R^1$ includes for example aryl with 6 to carbon atoms. Specifically, the aryl includes for example phenyl, α-naphthyl, and β-naphthyl. Among them, phenyl is particularly preferable.

The alkylene of $R^2$ is not particularly limited to the form of straight or branched chain, and includes for example alkylene with one to 6 carbon atoms. Specifically, the alkylene includes for example methylene, ethylene, trimethylene, tetramethylene, pentamethylene, hexamethylene, 2-(ethyl)trimethylene, and 1-(methyl)tetramethylene.

Ribose modification at other positions includes for example modification at the 4'-position to prepare thio-ribose. Modification of the phosphate backbones includes for example modifications thereof to prepare phosphorothioate, phosphorodithioate, alkylphosphonate or phosphoroamidate.

The weight ratio (the carrier of the present invention/the pharmaceutical agent) of the carrier of the present invention and the pharmaceutical agent to be contained in the composition of the present invention varies, depending on the type of the pharmaceutical agent and the formulating ratio of the derivative of the present invention and Compound A in the carrier of the present invention. The weight ratio thereof is appropriately within a range of 0.01 to 1,000, and is preferably within a range of 10 to 300 and more preferably within a range of 100 to 200. In case that the pharmaceutical agent contained therein is an oligonucleic acid, the weight ratio is appropriately within a range of 0.01 to 100, and is preferably within a range of 1 to 50 and more preferably within a range of 5 to 30.

In addition to the carrier of the present invention and the pharmaceutical agent, appropriate pharmaceutically acceptable additives may be blended in the composition of the present invention. Such additives include for example auxiliary emulsification agents (for example, fatty acids with 6 to 22 carbon atoms and pharmaceutically acceptable salts thereof, albumin, dextran), stabilizers (for example, cholesterol, phophatidic acid), isotonic agents (for example, sodium chloride, glucose, maltose, lactose, sucrose, trehalose), and pH adjusters (for example, hydrochloric acid, sulfuric acid, phosphoric acid, acetic acid, sodium hydroxide, potassium hydroxide, triethanolamine). These may be used singly or in combination of two or more thereof. The content of the additives in the composition of the present invention is appropriately 90% by weight or less, preferably 70% by weight or less and more preferably 50% by weight or less.

The composition of the present invention can be prepared by adding a pharmaceutical agent to a dispersion of the carrier of the present invention and appropriately agitating the resulting dispersion. In the course of producing the carrier of the present invention, a pharmaceutical agent is added to prepare the composition of the present invention. The additives may be added at an appropriate time of the process either before or after a dispersion treatment.

The composition of the present invention may be prepared as a liquid preparation or a freeze-dried preparation. In case of a liquid preparation, the concentration of the carrier of the present invention contained in the composition of the present invention is appropriately within a range of 0.001 to 50 w/v %, and is preferably within a range of 0.01 to 25 w/v % and more preferably within a range of 0.1 to 10 w/v %.

According to a conventional method, the freeze-dried preparation can be prepared by subjecting the composition of the present invention in a form of the liquid preparation to a freeze-drying process. After the composition of the present invention in the form of a liquid preparation is appropriately sterilized, for example, a given volume is divided in a vial, for preliminary freezing under conditions of about −40 to −20° C. for about 2 hours, followed by primary drying at reduced pressure at about 0 to 10° C. and secondary drying under reduced pressure at about 15 to 25° C., to freeze-dry the preliminarily freeze-dried preparation. Generally, the inside of the vial is replaced with nitrogen gas; then, the vial is covered with a stopper to prepare the freeze-dried preparation of the composition of the present invention.

The freeze-dried preparation of the composition of the present invention is used after the freeze-dried preparation is again dissolved in an appropriate solution (solution for re-dissolution), which is preliminarily added to the freeze-dried preparation. Such solution for re-dissolution includes for example distilled water for injections, physiological saline and other general infusions. The volume of such solution for re-dissolution varies depending on the use. With no specific limitation, the volume is appropriately 0.5 to 2-fold the volume of the composition of the present invention before freeze-drying or is 500 mL or less.

The composition of the present invention may be used for therapeutic treatments of for example cancer, viral diseases, inflammatory diseases, metabolic diseases and nerve diseases.

The composition of the present invention may be administrated at any pharmaceutically acceptable dosing form, with no specific limitation. The dosing form may be selected depending on the therapeutic method. The dosing form includes for example intravenous administration, intra-arterial administration, oral administration, transpulmonary administration, intra-tissue administration, trans-dermal administration, mucosal administration, intra-rectal administration, intra-bladder administration, intraperitoneal administration, ocular administration, intra-cerebral administration and intra-thoracic administration. Among them, in particular, intravenous administration, trans-dermal administration and mucosal administration are preferable. The dosage form of the composition of the present invention is not particularly limited, and include, for example, various injections, oral agents, infusions, inhalations, eye drops, ointments, lotions and suppositories.

The dose of the composition of the present invention as a pharmaceutical agent is preferably adjusted, taking into account the type and dosage form of the pharmaceutical agent and the patient conditions such as age and body weight, the dosing form, and the conditions and level of the disease. Generally, the dose is within a range of 0.01 mg to 10 g/human/day, and is preferably within a range of 0.1 mg to 5 g/human/day as the dose of the pharmaceutical agent per adult. In case that the pharmaceutical agent contained in the composition of the present invention is an oligonucleic acid, generally, the dose of the oligonucleic acid per adult is within a range of 0.1 mg to 10 g/human/day, and is preferably within a range of 1 mg to 5 g/human/day. The numerical figures sometimes vary depending on the target disease type, the dosing form and the target molecule. Therefore, in some cases, the dose of the oligonucleic acid may be satisfactorily below the range described above. In other cases, a dose above the range described above may be needed. The dose may be administered once daily or several times a day or may be administered at an interval of one day to several days.

EXAMPLES

The present invention is now described in detail with reference to Production Examples, Examples, Comparative Examples and Test Examples. However, the present invention is never limited to the scope described in the Examples.

Production Example 1

Synthetic Preparation of Oligo RNA

Using an automatic nucleic acid synthesizer (Expedite 8909; manufactured by Applied BioSystems), oligo RNA of the nucleotide sequence of SQ ID No.1, oligo RNA of the nucleotide sequence of SQ ID No.2, oligo RNA of the nucleotide sequence of SQ ID No.3, oligo RNA of the nucleotide sequence of SQ ID No.4, oligo RNA of the nucleotide sequence of SQ ID No.5, and oligo RNA of the nucleotide sequence of SQ ID No.6 were synthetically prepared according to the amidite method described in Nucleic Acid Research, 1984, Vol. 12, p. 4539-4557.

Protective groups of the nucleotides were removed by cleavage at CPG with a mixture solution of concentrated ammonium hydroxide and ethanol (3/1) and a reaction in the same solution at 55° C. for 18 hours. Subsequently, a reaction with a tetrahydrofuran solution of 1M tetrabutylammonium fluoride at ambient temperature for 20 hours deprotected the silyl group at the 2'-position. The resulting oligo RNA was purified by reverse-phase chromatography. After a reaction using aqueous 80% acetic acid solution at ambient temperature for 30 minutes deprotected dimethoxytrityl group at the 5'-position, the resulting product was again purified by ion exchange chromatography. The resulting concentrations of oligo RNA of the nucleotide sequence of SQ ID No.1, oligo RNA of the nucleotide sequence of SQ ID No.2, oligo RNA of the nucleotide sequence of SQ ID No.3, oligo RNA of the nucleotide sequence of SQ ID No.4, oligo RNA of the nucleotide sequence of SQ ID No.5 and oligo RNA of the nucleotide sequence of SQ ID No.6 were 9.99 mg/ml, 9.99 mg/ml, 3.37 mg/ml, 3.45 mg/ml, 2.74 mg/ml and 3.20 mg/ml, respectively.

It was confirmed by capillary electrophoresis that 90% of the resulting oligo RNAs had a chain length of 21 nucleotides.

Production Example 2

Synthetic Preparation of Tritium-Labeled Oligo RNA

A tritium-labeled oligo double-stranded RNA comprising oligo RNA of the nucleotide sequence of SQ ID No.3 and oligo RNA of the nucleotide sequence of SQ ID No.4 was synthetically prepared via incorporation of tritium-labeled [25'8-3H]adenosine 5'-triphosphate ammonium salt (manufactured by Amersham BioScience), using in vitro Transcription T7 Kit (manufactured by Takara-Bio Co., Ltd.).

Subsequently, proteins were removed from the oligo double-stranded RNA, using a phenol/chloroform mixture solution; and subsequently using a G-25 spin column (manufactured by Pharmacia), further, unreactive monomers were removed. The oligo double-stranded RNA was at a concentration of 1.65 mg/ml. Additionally, the specific radioactivity was $5.8 \times 10^5$ dpm/µg.

It was confirmed by 15% polyacrylamide electrophoresis that the resulting oligo RNA had a chain length around 21 base pairs.

Example 1

Synthetic preparation of 2-O-(methoxypolyethylene glycol propyl)carbamoyl-1,3-O-dioleoylglycerol Step 1

Synthetic preparation of 1,3-dioleoylglycerol 3.8 g of dihydroxyacetone dimer, 25 g of oleic acid, g of 1-ethyl-3-(3-dimethylaminopropyl)carbodiimide hydrochloride salt, and 12.9 g of 4-dimethylaminopyridine were dissolved in 150 mL of dichloromethane, for reaction under agitation at ambient temperature for 4 hours. The organic layer was washed by adding aqueous 0.5 M potassium dihydrogen phosphate solution to the reaction solution. After the organic layer was dried and concentrated under reduced pressure, 1 L of methanol was added to the resulting residue; the generated powder was filtered and recovered, and then dried. The dried powder was dissolved in a mixture solution of 170 mL of tetrahydrofuran and 17 mL of aqueous 10% acetic acid solution, to which 1.7 g of sodium borohydride was added in small portions at 0° C. Subsequently, the resulting mixture was agitated at ambient temperature for 2 hours to promote the reaction. The resulting reaction solution was poured in saturated aqueous sodium hydrogen carbonate, for extraction with ethyl acetate. After the organic layer was dried, the organic layer was concentrated under reduced pressure. The residue was purified by silica gel column chromatography, to obtain 14.5 g of the intended product.
MALTI-TOF Mass (m/z)=643.320 ([M+Na]$^+$)

Step 2

Synthetic preparation of 2-O-(methoxypolyethylene glycol propyl)carbamoyl-1,3-O-dioleoylglycerol 3.4 g of 1,3-dioleoylglycerol obtained above in the step 1 was dissolved in 30 ml of pyridine; 1.7 g of N,N'-carbonyldiimidazole was added to the resulting solution, for overnight reaction under agitation at ambient temperature. After concentrating the resulting reaction solution under reduced pressure, the resulting residue was dissolved in dichloromethane; to the resulting solution was added aqueous 5% sodium dihydrogen phosphate for washing the organic layer. After the organic layer was dried, the organic layer was concentrated under reduced pressure. 920 mg of the resulting residue was dissolved in 10 mL of pyridine; to the resulting solution was added 3.39 g of α-aminopropyl-ω-methoxypolyoxyethylene [SUNBRIGHT (under trade mark) MEPA-20H; manufactured NOF Corporation: hereafter the same is applied], for overnight reaction under agitation at 40° C. After the reaction solution was concentrated under reduced pressure, the resulting solution was coevaporated three times with toluene. The residue was purified by silica gel column chromatography, to obtain 2.9 g of the entitled derivative of the present invention.

The molecular weight thereof was analyzed by mass spectrometry using the electrospray ionization method. As shown in FIG. 1, consequently, the molecular weight of the derivative of the present invention was distributed within a range from 2,200 to 3,500.

Example 2

Synthetic preparation of 2-O-(methoxypolyethylene glycol propyl)carbamoyl-1,3-O-distearoylglycerol Step 1

Synthetic preparation of 1,3-distearoylglycerol 3.0 g of dihydroxyacetone dimer, 22.7 g of stearic acid, 16.8 g of 1-ethyl-3-(3-dimethylaminopropyl)carbodiimide hydrochloride salt, and 10.8 g of 4-dimethylaminopyridine were dissolved in 100 mL of dichloromethane, for overnight reaction under agitation at ambient temperature. Adding 0.5 L of methanol to the reaction solution, the generated powder was filtered and recovered. The powder recovered by filtration was washed with methanol. After the washed powder was dried, 6 g of the dried powder was dissolved in a mixture solution of 400 mL of tetrahydrofuran and 20 mL of aqueous 10% acetic acid solution, to which 1.1 g of sodium borohydride was added in small portions at 0° C. Subsequently, the resulting mixture was agitated at ambient temperature for 6 hours to promote the reaction. The resulting reaction solution was poured in saturated aqueous sodium hydrogen carbonate, for extraction in ethyl acetate. After the organic layer was dried, the organic layer was concentrated under reduced pressure. The residue was purified by silica gel column chromatography, to obtain 3.5 g of the intended product.
MALTI-TOF Mass (m/z)=647.547 ([M+Na]$^+$)

Step 2

Synthetic preparation of 2-O-(methoxypolyethylene glycol propyl)carbamoyl-1,3-O-distearoylglycerol 0.4 g of 1,3-distearoylglycerol obtained above in the step 1 was dissolved in 10 ml of pyridine; 156 mg of N,N'-carbonyldiimidazole was added to the resulting solution, for overnight reaction under agitation at ambient temperature. After concentrating the resulting reaction solution under reduced pressure, the resulting residue was dissolved in dichloromethane; to the resulting solution was added aqueous 5% sodium dihydrogen phosphate for washing the organic layer. After the organic layer was dried, the organic layer was concentrated under reduced pressure. 450 mg of the resulting residue was dissolved in a mixture solution of 10 mL of pyridine and 4 mL of dichloromethane; to the resulting solution was added 1.64 g of α-aminopropyl-ω-methoxypolyoxyethylene, for overnight reaction under agitation at 40° C. After the reaction solution was concentrated under reduced pressure, the resulting solution was co-boiled three times with toluene. The residue was purified by silica gel column chromatography, to obtain 1.2 g of the entitled derivative of the present invention.

Figure 2:
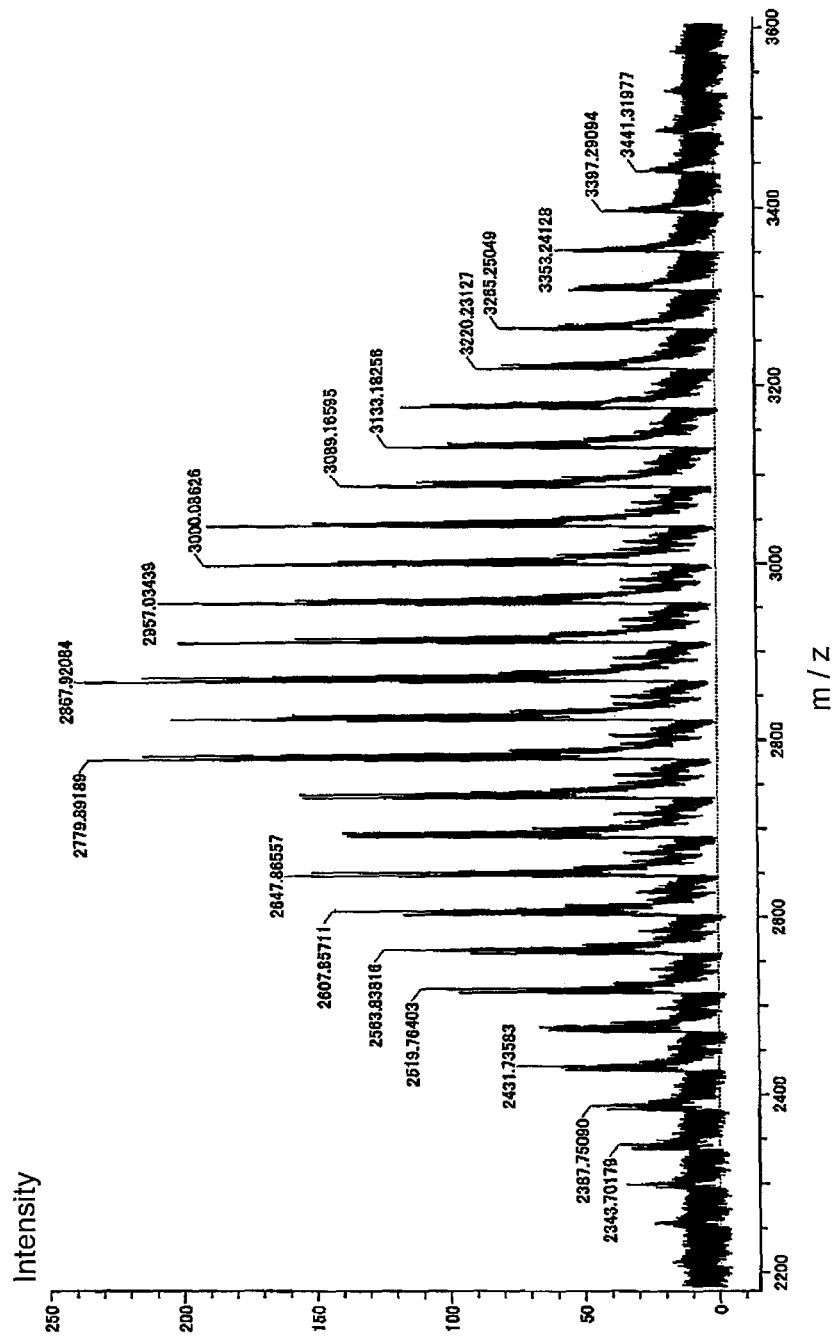
FIG. 2 shows the mass spectrum of the derivative of the present invention synthetically prepared in Example 2.

The molecular weight thereof was analyzed by mass spectrometry using the electrospray ionization method. As shown in FIG. 2, consequently, the molecular weight of the derivative of the present invention was distributed within a range from 2,200 to 3,500.

Example 3

Preparation of Dispersion of the Carrier of the Present Invention 60 mg of Compound A, 8 mg of the derivative of the present invention synthetically prepared in Example 1, and mg of egg yolk lecithin (manufactured by Q.P. Corporation; hereafter the same is applied) were dissolved in 2 mL of chloroform in a vial, to which nitrogen gas was purged for removing chloroform to form a thin film on the wall face of the vial. After the vial was left to stand overnight at reduced pressure, 1,000 mg of maltose (manufactured by Otsuka Pharmaceutical Co., Ltd.; hereafter the same is applied), 4.0 mL of distilled water for injections (manufactured by Otsuka Pharmaceutical Co., Ltd.; hereafter the same is applied) and 81 µL of 1N hydrochloric acid were added to the vial. The thin film was dispersed with a vortex mixer. After the dispersion was left to stand at 4° C. for 3 hours, the dispersion was treated by ultrasonication using a microprobe for 10 minutes, to prepare a dispersion of the carrier of the present invention at 32 mg/mL. Using distilled water for injections, the dispersion was adjusted to 5.0 mL.

Example 4

Preparation of Dispersion of the Carrier of the Present Invention

A dispersion of the carrier of the present invention was prepared in the same manner as in Example 3, using 60 mg of Compound A, 32 mg of the derivative of the present invention synthetically prepared in Example 1 and 68 mg of egg yolk lecithin.

Example 5

Preparation of Dispersion of the Carrier of the Present Invention

A dispersion of the carrier of the present invention was prepared in the same manner as in Example 3, using 60 mg of Compound A, 80 mg of the derivative of the present invention synthetically prepared in Example 1 and 20 mg of egg yolk lecithin.

Example 6

Preparation of the Composition of the Present Invention (1) Preparation of Nucleic Acid Solution By mixing together 0.50 mL of a solution of the oligo RNA of the nucleotide sequence of SQ ID NO.1 as prepared in Production Example 1, 0.50 mL of a solution of the oligo RNA of the nucleotide sequence of SQ ID NO.2 as prepared in Production Example 1, and 4.00 mL of distilled water for injections, a nucleic acid solution was prepared.

(2) Preparation of the Composition of the Present Invention 5 mL of the dispersion of the carrier of the present invention as prepared in Example 4 was added to the whole volume of the nucleic acid solution prepared above in (1), for ultrasonic treatment for 5 minutes. After the resulting solution was centrifuged at 5,000 rpm for 20 minutes and filtered through a 0.22-µm filter, the composition of the present invention at 1.0 mg/mL was prepared.

(3) Assay of Mean Particle Size of Drug Carrier

The mean particle size of the drug carrier in the composition of the present invention was assayed by diluting the composition of the present invention prepared above in (2) to 0.02 mg/mL, using distilled water for injections. Specifically, the mean particle size thereof was assayed in triplicate, using a particle size meter [Nicomp C380 (under trade name): Particle Sizing Systems, Inc.; hereafter the same is applied] while presetting the refractive index to 0.993, the viscosity to 1.333 and the assay time period to 5 minutes. Consequently, the mean particle size of the drug carrier in the composition of the present invention was 97.6 nm.

Example 7

Preparation of the Composition of the Present Invention (1) Preparation of Nucleic Acid Solution In the same manner as described above in Example 6, (1), a nucleic acid solution was prepared.

(2) Preparation of the Composition of the Present Invention

Using the whole volume of the nucleic acid solution prepared above in (1) and 5 mL of the dispersion of the carrier of the present invention as prepared in Example 5, the composition of the present invention at 1.0 mg/mL was prepared in the same manner as in Example 6, (2).

The mean particle size of the drug carrier in the composition of the present invention was measured by the same method as in Example 6, (3). The mean particle size thereof was 47.1 nm.

Example 8

Preparation of Dispersion of the Carrier of the Present Invention

Using 60 mg of Compound A, 80 mg of the derivative of the present invention synthetically prepared in Example and 20 mg of egg yolk lecithin, a dispersion of the carrier of the present invention was prepared as in Example 3.

Example 9

Preparation of Dispersion of the Carrier of the Present Invention

Using 60 mg of Compound A, 32 mg of the derivative of the present invention synthetically prepared in Example and 68 mg of cholesterol (manufactured by Wako Pure Chemical Industries, Ltd.; hereafter the same is applied), a dispersion of the carrier of the present invention was prepared as in Example 3.

Example 10

Preparation of Dispersion of the Carrier of the Present Invention

Using 60 mg of Compound A, 80 mg of the derivative of the present invention synthetically prepared in Example 1 and 20 mg of cholesterol, a dispersion of the carrier of the present invention was prepared as in Example 3.

Example 11

Preparation of Dispersion of the Carrier of the Present Invention

Using 60 mg of Compound A, 32 mg of the derivative of the present invention synthetically prepared in Example 2 and 68 mg of cholesterol, a dispersion of the carrier of the present invention was prepared as in Example 3.

Example 12

Preparation of Dispersion of the Carrier of the Present Invention

Using 60 mg of Compound A, 80 mg of the derivative of the present invention synthetically prepared in Example 2 and 20 mg of cholesterol, a dispersion of the carrier of the present invention was prepared as in Example 3.

Example 13

Preparation of the Composition of the Present Invention (1) Preparation of Nucleic Acid Solution
By mixing together 0.50 mL of a solution of the oligo RNA of the nucleotide sequence of SQ ID NO.1 as prepared in Production Example 1, 0.50 mL of a solution of the oligo RNA of the nucleotide sequence of SQ ID NO.2 as prepared in Production Example 1, and 4.00 mL of distilled water for injections, a nucleic acid solution was prepared.
(2) Preparation of the Composition of the Present Invention
Using the whole volume of the nucleic acid solution prepared above in (1) and 5 mL of the dispersion of the carrier of the present invention as prepared in Example 8, the composition of the present invention at 1.0 mg/mL was prepared in the same manner as in Example 6, (2).
Herein, the mean particle size of the drug carrier in the composition of the present invention was assayed in the same manner as in Example 6, (3), which was 41.6 nm.

Example 14

Preparation of the Composition of the Present Invention (1) Preparation of Nucleic Acid Solution
In the same manner as described above in Example 13, (1), a nucleic acid solution was prepared.
(2) Preparation of the Composition of the Present Invention
Using the whole volume of the nucleic acid solution prepared above in (1) and 5 mL of the dispersion of the carrier of the present invention as prepared in Example 9, the composition of the present invention at 1.0 mg/mL was prepared in the same manner as in Example 6, (2).
The mean particle size of the drug carrier in the composition of the present invention was measured by the same method as in Example 6, (3). The mean particle size thereof was 131.4 nm.

Example 15

Preparation of the Composition of the Present Invention (1) Preparation of Nucleic Acid Solution
In the same manner as described above in Example 13, (1), a nucleic acid solution was prepared.
(2) Preparation of the Composition of the Present Invention
Using the whole volume of the nucleic acid solution prepared above in (1) and 5 mL of the dispersion of the carrier of the present invention as prepared in Example 10, the composition of the present invention at 1.0 mg/mL was prepared in the same manner as in Example 6, (2).
The mean particle size of the drug carrier in the composition of the present invention was measured by the same method as in Example 6, (3). The mean particle size thereof was 46.3 nm.

Example 16

Preparation of the Composition of the Present Invention (1) Preparation of Nucleic Acid Solution
In the same manner as described above in Example 13, (1), a nucleic acid solution was prepared.
(2) Preparation of the Composition of the Present Invention
Using the whole volume of the nucleic acid solution prepared above in (1) and 5 mL of the dispersion of the carrier of the present invention as prepared in Example 11, the composition of the present invention at 1.0 mg/mL was prepared in the same manner as in Example 6, (2).
The mean particle size of the drug carrier in the composition of the present invention was measured by the same method as in Example 6, (3). The mean particle size thereof was 140.4 nm.

Example 17

Preparation of the Composition of the Present Invention (1) Preparation of Nucleic Acid Solution
In the same manner as described above in Example 13, (1), a nucleic acid solution was prepared.
(2) Preparation of the Composition of the Present Invention
Using the whole volume of the nucleic acid solution prepared above in (1) and 5 mL of the dispersion of the carrier of the present invention as prepared in Example 12, the composition of the present invention at 1.0 mg/mL was prepared in the same manner as in Example 6, (2).
The mean particle size of the drug carrier in the composition of the present invention was measured by the same method as in Example 6, (3). The mean particle size thereof was 48.3 nm.

Example 18

Preparation of the Composition of the Present Invention (1) Preparation of Nucleic Acid Solution By mixing together 36 μL of the solution of the tritium-labeled oligo double-stranded RNA prepared in Production Example 2, 1.50 mL of the solution of the oligo RNA of the nucleotide sequence of SQ ID NO.3 as prepared in Production Example 1, 1.43 mL of the solution of the oligo RNA of the nucleotide sequence of SQ ID NO.4 as prepared in Production Example 1, and 2.07 mL of distilled water for injections, a nucleic acid solution was prepared.

(2) Preparation of the Composition of the Present Invention

Using the whole volume of the nucleic acid solution prepared above in (1) and 5 mL of the dispersion of the carrier of the present invention as prepared in Example 9, the composition of the present invention at 1.0 mg/mL was prepared in the same manner as in Example 6, (2).

The mean particle size of the drug carrier in the composition of the present invention was assayed by the same method as in Example 6, (3), which was 120.5 nm.

Example 19

Preparation of the Composition of the Present Invention (1) Preparation of Nucleic Acid Solution By mixing together 1.88 mL of the solution of the oligo RNA of the nucleotide sequence of SQ ID NO.5 as prepared in Production Example 1, 1.52 mL of the solution of the oligo RNA of the nucleotide sequence of SQ ID NO.6 as prepared in Production Example 1, and 1.61 mL of distilled water for injections, a nucleic acid solution was prepared.

(2) Preparation of the Composition of the Present Invention

Using the whole volume of the nucleic acid solution prepared above in (1) and 5 mL of the dispersion of the carrier of the present invention as prepared in Example 9, the composition of the present invention at 1.0 mg/mL was prepared in the same manner as in Example 6, (2).

The mean particle size of the drug carrier in the composition of the present invention was assayed by the same method as in Example 6, (3), which was 165.0 nm.

Comparative Example 1

Preparation of Dispersion of Carrier as Comparative Control

Using 60 mg of Compound A and 100 mg of egg yolk lecithin, a dispersion of a carrier as a comparative control was prepared in the same manner as in Example 3.

Comparative Example 2

Preparation of Dispersion of Carrier as Comparative Control

Using 60 mg of Compound A, and 32 mg of N-(methoxy polyethylene glycol carbonyl)distearoyl phosphatidylethanolamine of a mean molecular weight of 2, 898 [SUNBRIGHT (under trade name) DSPE-020CN: manufactured by NOF Corporation] (hereinafter, referred to as "Compound B") and 68 mg of egg yolk lecithin, a dispersion of a carrier as a comparative control was prepared in the same manner as in Example 3.

Figure 3:
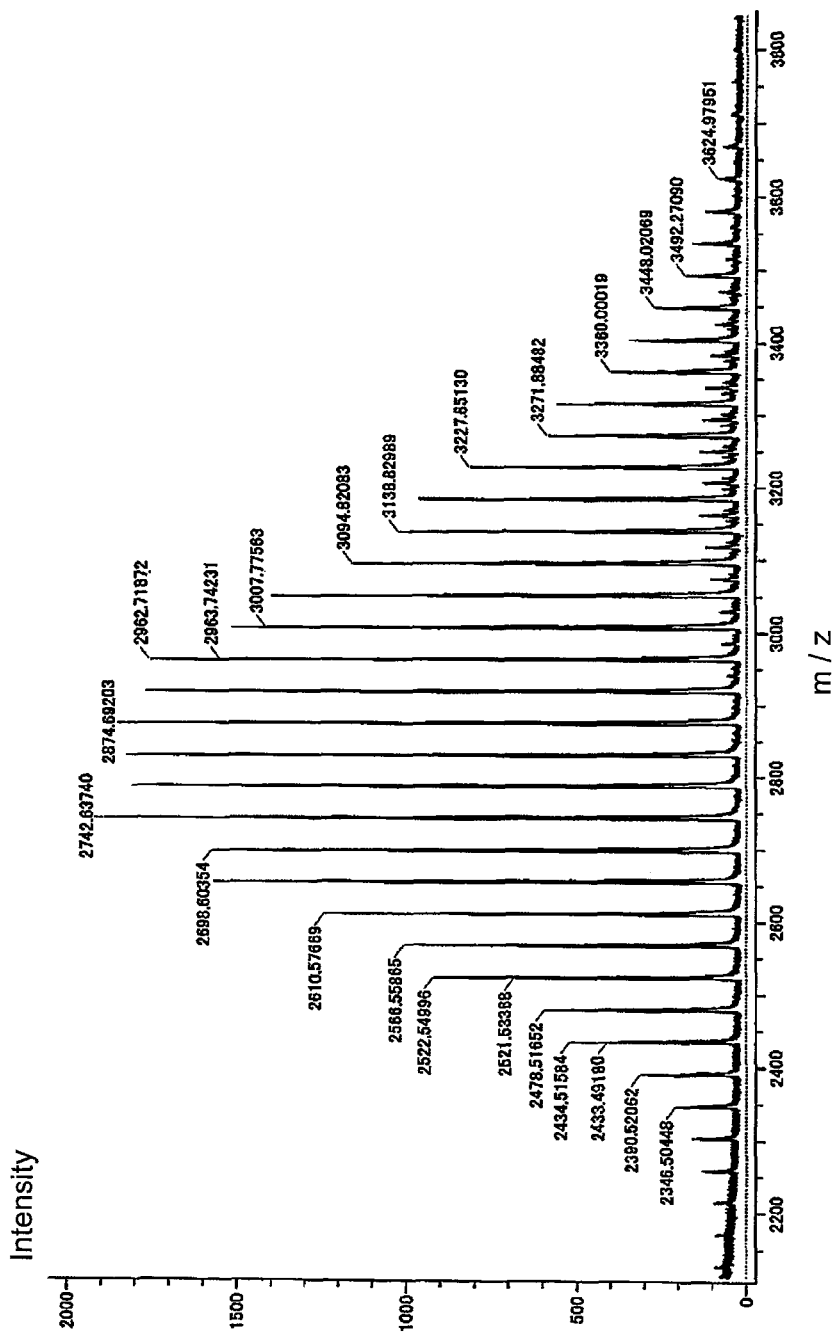
FIG. 3 shows the mass spectrum of Compound B used in Comparative Examples 2 and 3.

The molecular weight thereof was determined by mass spectrometry using the electrospray ionization method. As shown in FIG. 3, consequently, the molecular weight of Compound B used was distributed within a range from 2,100 to 3,800.

Comparative Example 3

Preparation of Dispersion of Carrier as Comparative Control

Using 60 mg of Compound A, 80 mg of Compound B and 20 mg of egg yolk lecithin, a dispersion of a carrier as a comparative control was prepared in the same manner as in Example 3.

Comparative Example 4

Preparation of Dispersion of Carrier as Comparative Control

Using LIPOFECTIN® (manufactured by Invitrogen), a dispersion of a carrier as a comparative control was prepared by the method instructed by the supply company.

Comparative Example 5

Preparation of Dispersion of Carrier as Comparative Control

Using OLIGOFECTOAMINE™ (manufactured by Invitrogen), a dispersion of a carrier as a comparative control was prepared by the method instructed by the supply company.

Comparative Example 6

Preparation of Composition as Comparative Control (1) Preparation of Nucleic Acid Solution A nucleic acid solution was prepared in the same manner as in Example 6, (1).

(2) Preparation of Composition as a Comparative Control

Using the whole volume of the nucleic acid solution prepared above in (1) and 5 mL of the dispersion of the carrier as a comparative control as prepared in Comparative Example 1, a composition at 1.0 mg/mL as a comparative control was prepared in the same manner as in Example 6, (2).

The mean particle size of the drug carrier in the composition as a comparative control was assayed by the same method as in Example 6, (3), which was 138.6 nm.

Comparative Example 7

Preparation of Composition as Comparative Control (1) Preparation of Nucleic Acid Solution A nucleic acid solution was prepared in the same manner as in Example 6, (1).

(2) Preparation of Composition as a Comparative Control

Using the whole volume of the nucleic acid solution prepared above in (1) and 5 mL of the dispersion of the carrier as a comparative control as prepared in Comparative Example 2, a composition at 1.0 mg/mL as a comparative control was prepared in the same manner as in Example 6, (2).

The mean particle size of the drug carrier in the composition as a comparative control was assayed by the same method as in Example 6, (3), which was 106.9 nm.

Comparative Example 8

Preparation of Composition as Comparative Control (1) Preparation of Nucleic Acid Solution
A nucleic acid solution was prepared in the same manner as in Example 6, (1).
(2) Preparation of Composition as Comparative Control
Using the whole volume of the nucleic acid solution prepared above in (1) and 5 mL of the dispersion of the carrier as a comparative control as prepared in Comparative Example 3, a composition at 1.0 mg/mL as a comparative control was prepared in the same manner as in Example 6, (2).
The mean particle size of the drug carrier in the composition as a comparative control was assayed by the same method as in Example 6, (3), which was 93.0 nm.

Comparative Example 9

Preparation of Composition as Comparative Control (1) Preparation of Nucleic Acid Solution
A nucleic acid solution was prepared in the same manner as in Example 13, (1).
(2) Preparation of Composition as Comparative Control
Using the whole volume of the nucleic acid solution prepared above in (1) and 5 mL of the dispersion of the carrier as a comparative control as prepared in Comparative Example 1, a composition at 1.0 mg/mL as a comparative control was prepared in the same manner as in Example 6, (2).
The mean particle size of the drug carrier in the composition as a comparative control was assayed by the same method as in Example 6, (3), which was 151.0 nm.

Test Example 1

Evaluation of Hemolytic Property of the Carrier of the Present Invention (1) Experimental Method
Blood drawn from a male rat (Slc: SD, 7-week-old; Japan SLC, Inc.) was centrifuged at 3,000 rpm for 10 minutes, from which the upper layer was removed to obtain a suspension of erythrocytes. To the resulting erythrocyte suspension was added a 2-fold volume of physiological saline for injections (manufactured by Otsuka Pharmaceutical Factory, Inc.; hereafter the same is applied). The resulting mixture was mixed together and subsequently centrifuged at 3,000 rpm for 5 minutes. The procedure was additionally repeated two more times. The resulting erythrocyte suspension was diluted to $1 \times 10^9$ cells/mL, using physiological saline for injections.
The carrier dispersions prepared in Examples 5 and 8 or in Comparative Examples 1, 3, 4 and 5 were diluted with % maltose, to desired concentrations within a range from 0.3 μg/μL to 30 mg/μL. After 285 μL of each diluted carrier dispersion was preliminarily heated at 37° C. for 10 minutes, 15 μL of the erythrocyte suspension was added for incubation at 37° C. for 30 minutes. The reaction solution was centrifuged at 3,000 rpm for 3 minutes, to recover the supernatant. The absorbance of the supernatant at 405 nm was measured.
Hemolytic level was calculated with the absorbance without any carrier added defined as 0-% hemolysis level and the absorbance with addition of 0.02% Triton X100 defined as 100-% hemolytic level. Additionally, the concentration causing 50% hemolysis (hereinafter, designated as "50-% hemolysis concentration") was calculated on the basis of the calculated hemolytic level.
(2) Experimental Results
As shown in Table 1, the 50-% hemolysis concentrations of the carriers of the present invention in Examples 5 and 8 were higher than the 50-% hemolysis concentrations of the carriers as comparative controls in Comparative Examples 1, 3, 4 and 5.

TABLE 1

|  | 50-% hemolysis concentration (μg/mL) |
| --- | --- |
| Example 5 | >30,000 |
| Example 8 | >30,000 |
| Comparative Example 1 | 50.8 |
| Comparative Example 3 | 14,500 |
| Comparative Example 4 | 1.0 |
| Comparative Example 5 | 1.6 |

Test Example 2

Evaluation of Cytotoxicity of the Carrier of the Present Invention (1) Experimental Method
Endothelial cells of human cord vein (manufactured by Sanko Jyunyaku Co., Ltd.) were inoculated in a 96-well plate to 3,000 cells/well, for overnight culture. The carrier dispersion prepared in Example 5 or Comparative Examples 1, 3, 4 or 5 was diluted with 10% maltose, to a desired concentration within a range from 3 μg/μL to 10 mg/μL. The diluted carrier dispersion was added at a 1/10-fold volume of the culture medium. After culturing for 72 hours, viable cells were counted with Cell Counting Kit-8 (WST-8: manufactured by Dojin Chemical Co., Ltd.). Based on the resulting number, the concentration inhibiting the growth of 50% of the cells was calculated. Additionally, the culture medium M199 (manufactured by Nissui Pharmaceutical Co., Ltd.) was used to culture the endothelial cells of human cord vein.
(2) Experimental Results
As shown in Table 2, the 50-% cell growth-inhibiting concentration of the carrier of the present invention in Example 5 was higher than the 50-% cell growth-inhibiting concentrations of the carriers as comparative controls in Comparative Examples 1, 3, 4 and 5.

TABLE 2

|  | 50-% cell growth-inhibiting concentration (μg/mL) |
| --- | --- |
| Example 5 | >1,000 |
| Comparative Example 1 | 151.1 |
| Comparative Example 3 | 627.6 |
| Comparative Example 4 | 6.7 |
| Comparative Example 5 | 15.2 |

Test Example 3

Evaluation of Cytokine Induction Potency of the Composition of the Present Invention (1) Experimental Method
The compositions prepared in Examples 6 and 7 or Comparative Examples 6, 7 and 8 were given at a dose of 10 mL/kg into the tail veins of male mice (C57BL/6J, aged 6 weeks; CLEA Japan, Inc.). Two hours after the administration, whole blood was drawn out of the abdominal aorta of the mice under anesthesia with Ethrane, to prepare serum. Three mice were used per one group. As a negative control, mice without any treatment were used.

Serum IFN-α concentration was assayed with Mouse Interferon Alpha ELISA kit (manufactured by PBL).

(2) Experimental Results

As shown in Table 3, the IFN-α levels induced via the administration of the compositions of the present invention in Examples 6 and 7 were lower than the IFN-α levels induced via the administration of the compositions as comparative controls in Comparative Examples 6, 7, and 8. Depending on the concentration of the derivative of the present invention in Example 1, additionally, the IFN-α level induced was decreased.

TABLE 3

|  | IFN-α concentration (pg/mL) Mean ± standard deviation |
| --- | --- |
| Negative Control | 14.8 ± 6.5 |
| Example 6 | 192.0 ± 73.0 |
| Example 7 | 20.2 ± 7.3 |
| Comparative Example 6 | 525.4 ± 156.4 |
| Comparative Example 7 | 677.0 ± 222.8 |
| Comparative Example 8 | 964.6 ± 271.3 |

Test Example 4

Evaluation of Cytokine Induction Potency of the Composition of the Present Invention (1) Experimental Method Human fresh blood was collected. So as to avoid coagulation, a heparin sodium injection (manufactured by Ajinomoto Co., Ltd.) at 1 mL/10 mL of blood was mixed therein. An equal volume of phosphate buffered saline (hereinafter, referred to as "PBS") was added; 10 mL of blood per 3 mL of Ficoll-Paque PLUS (manufactured by GE Healthcare BioSciences) were overlaid gently to avoid disruption of the interface. Peripheral monocytes were obtained by centrifugation at 400×g at ambient temperature for 30 minutes. The resulting peripheral monocytes were washed twice with PBS. Subsequently, the peripheral monocytes were suspended in an RPMI 1640 culture medium (manufactured by Nissui Pharmaceutical Co., Ltd.) containing 10% bovine fetal serum (manufactured by JRH BioSciences), 100 U/mL penicillin (manufactured by Nacalai Tesque, Inc.) and 100 μg/mL streptomycin (manufactured by Nacalai Tesque, Inc.), to count the cells therein to prepare a cell suspension at $2 \times 10^6$ cells/mL.

The cell suspension prepared was inoculated in a 48-well plate to 300 μL ($6 \times 10^5$ cells)/well, for culturing under conditions of 37° C. and 5% $CO_2$ for 3 hours. Then, the compositions prepared in Examples 7, 13, 14, 15, 16 and 17 or Comparative Example 9 were added to the culture medium to a desired concentration (30 nM or 100 nM). Cells were cultured for 24 hours after the composition was added. Subsequently, the culture supernatants were recovered for ELISA. IFN-α was assayed using the human interferon-alpha ELISA kit (manufactured by Bio Source).

(2) Experimental Results

As shown in Table 4, the IFN-α levels induced by treating the compositions of the present invention in Examples 7, 13, 14, 15, 16 and 17 were lower than the IFN-α level induced by treating the composition as a comparative control in Comparative Example 9.

TABLE 4

|  | Concentrations for the treatment | IFN-α concentration (pg/mL) |
| --- | --- | --- |
| Example 7 | 30 nM | <37.5 |
|  | 100 nM | <37.5 |
| Example 13 | 30 nM | <37.5 |
|  | 100 nM | <37.5 |
| Example 14 | 30 nM | <37.5 |
|  | 100 nM | 64 |
| Example 15 | 30 nM | <37.5 |
|  | 100 nM | <37.5 |
| Example 16 | 30 nM | <37.5 |
|  | 100 nM | 110 |
| Example 17 | 30 nM | <37.5 |
|  | 100 nM | <37.5 |
| Comparative Example 9 | 30 nM | 150 |
|  | 100 nM | 360 |

Test Example 5

Evaluation of Hepatic Deliverability of the Composition of the Present Invention (1) Experimental Method The composition of the present invention prepared in Example 18 was diluted to a nucleic acid concentration of 0.25 mg/mL in the composition of the present invention, which was then used in the following experiment.

Three or four male mice (C57BL/6J, aged 6 weeks; CLEA Japan, Inc.) were used per one group. The mice were divided into a group where blood was drawn 30 minutes after the administration of the composition of the present invention; a group where blood was drawn 2 hours after the administration of the composition of the present invention; a group where blood was drawn 8 hours after the administration of the composition of the present invention; and a group where blood was drawn 24 hours after the administration of the composition of the present invention. The composition of the present invention was given at a dose of 10 mL/kg into the tail veins of the mice in each of the groups. 30 minutes, 2 hours, 8 hours and 24 hours after the administration, blood was drawn out of the abdominal aortas of the mice under anesthesia with Ethrane; then, the animals were sacrificed. Subsequently, liver was resected to obtain the liver wet weight.

To the resected liver in a vial was added 1 mL of a tissue solubilizer (Solvable; manufactured by Perkin Elmer Co., Ltd.; the same is true hereinbelow), for shaking at 40° C. for two nights for solubilization. 10 mL of a scintilator (HionicFluor; manufactured by Perkin Elmer Co., Ltd.; hereafter the same is applied) was added to and mixed with the solubilized sample; using then a liquid scintillation counter, the radioactivity was assayed.

Based on the results, the distribution ratio (% of dose) of the composition of the present invention in liver was calculated.

(2) Experimental Results

Figure 4:
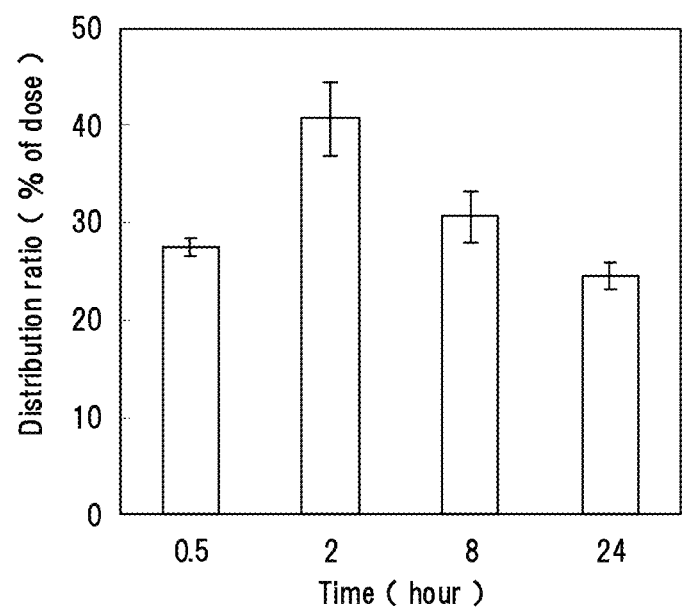
FIG. 4 shows hepatic deliverability. The vertical axis represents the distribution ratio (% of dose) of the composition while the horizontal axis represents the time period (in hours) after the administration of the composition of the present invention.

As shown in FIG. 4, the hepatic distribution ratio of the carrier of the present invention in the composition of the present invention in Example 18 was the highest 2 hours after the administration, just when about 40% of the total dose was delivered to liver.

Test Example 6

Evaluation of Hepatocytic Deliverability of the Composition of the Present Invention (1) Experimental Method Hepatocytes were separated according to the method described in Journal of Controlled Release, 2001, Vol. 70, p. 295-307.

The composition of the present invention prepared in Example 18 was administered at a dose of 10 mL/kg to 4 male mice (Slc: ddY, aged 8 weeks; Japan SLC, Inc.) into the tail vein.

Two hours after the administration, laparotomy was performed on the mice under anesthesia with pentobarbital. Perfusion with a buffer solution for preliminary perfusion was started from the portal vein. After it was confirmed that blood was replaced with the perfusion solution, the perfusion solution was exchanged to a collagenase solution. Perfusion was gradually carried out at a perfusion rate of about 2 mL/min for about 15 minutes, until the enzyme was activated to degrade hepatic lobule. The digested liver was transferred to a Petri dish and cut with scissors. After adding then a HANKS solution, the cells were suspended with a Komagome pipette. The resulting suspension was filtered through a gauze to prepare a cell suspension. The cell suspension was centrifuged at 50×g for 1.5 minutes, to recover the upper layer. The remaining precipitate was suspended in HANKS solution, passed through a 48-μm nylon mesh and centrifuged at 50×g for 1.5 minutes. Subsequently, the resulting precipitate was suspended in the HANKS solution and centrifuged at 50×g for 1.5 minutes. The procedure was repeatedly carried out twice more, to obtain hepatocytes. The upper layer recovered previously was centrifuged at 600×g for 5 minutes, to suspend the resulting precipitate in HANKS solution. The procedure was again carried out to obtain non-hepatocytic cells. The individual cell types were counted with a blood cell counter.

A small volume of the tissue solubilizer was added to 2.0 mL of each cell suspension, for overnight agitation at 40° C. for solubilization. 18 mL of the scintillator was added to and mixed with the solubilized sample; subsequently, the radioactivity was assayed with the liquid scintillation counter. Based on the results, the delivery level ($\mu g/10^7$ cells) of the composition of the present invention to the hepatocytes or non-hepatocytic cells per $10^7$ cells was calculated.

(2) Experimental Results

Figure 5:
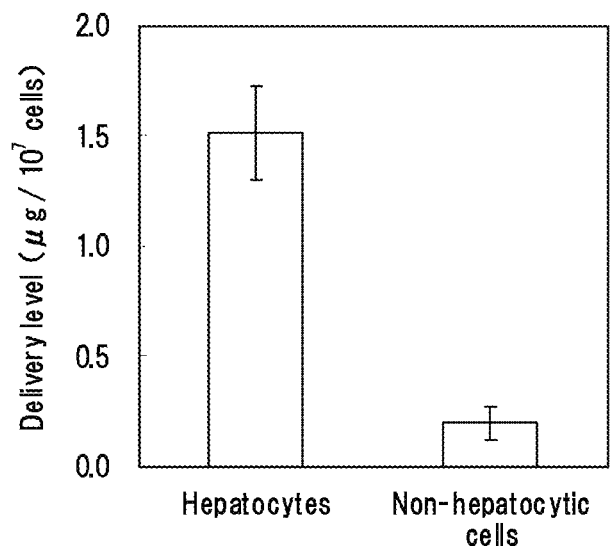
FIG. 5 shows the deliverability to hepatocytes and non-hepatocytic cells. The vertical axis represents the delivery level ($\mu$g/$10^7$ cells) of the composition of the present invention.

As shown in FIG. 5, the delivery level of the carrier of the present invention in the composition of the present invention in Example 18 to the hepatocytes was higher by about 8-fold than the delivery level to the non-hepatocytic cells.

Test Example 7

Evaluation of Liver Deliverability of the Composition of the Present Invention (1) The hepatic deliverability of the composition of the present invention was evaluated, using as the marker the effect of the oligo RNA in the composition of the present invention on suppressing the expression of a target gene. A nucleic acid comprising the oligo RNA of the nucleotide sequence of SQ ID NO.5 and the oligo RNA of the nucleotide sequence of SQ ID NO.6 as contained in the composition of the present invention prepared in Example 19 for use in this experiment is described as a nucleic acid suppressing the expression of SOD1 in Biochemical and Biophysical Research Communications, 2004, vol. 314, p. 283-291.

(2) Experimental Method

Four male mice (C57BL/6J, aged 6 weeks; CLEA Japan, Inc.) were used per one group. The mice were divided into three groups, namely a group for 2-day administration of the composition of the present invention; a group for 3-day administration of the composition of the present invention; and a group for 4-day administration of the composition of the present invention. The composition of the present invention prepared in Example 19 was given once daily at a dose of 10 mL/kg into the tail veins of the mice in each of the groups. 24 hours after the completion of the administration in each group, liver was resected, and frozen and stored in RNAlater® (manufactured by Ambion, Inc.). Subsequently, total RNA was extracted with Isogen (manufactured by Nippon Gene Co., Ltd.), to assay the SOD1 mRNA level in the RNA using QuantiGene 2.0 (manufactured by Panomics).

The resulting SOD1 mRNA level was corrected on the basis of the PPIB mRNA level in the mice livers. The SOD1 mRNA level in mice given 10% maltose instead of the composition of the present invention for 4 days was designated as 100% for evaluation.

(3) Experimental Results

Figure 6:
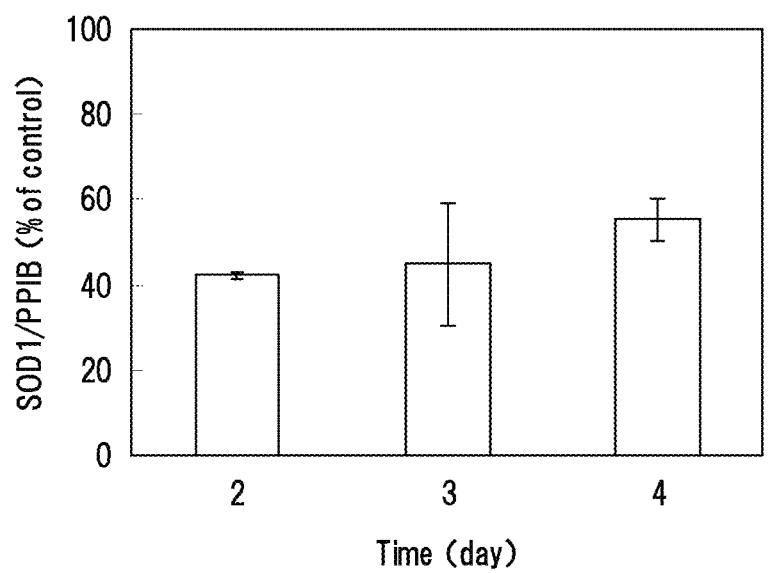
FIG. 6 shows the change of the superoxide dismutase 1 (SOD1) mRNA level in liver. The vertical axis represents the value (% of control) of SOD1 mRNA levels divided by the peptidyl-prolyl cic-trans isomerase B (PPIB) mRNA level, while the horizontal axis represents the time period (in days) after the administration of the composition of the present invention.

As shown in FIG. 6, the composition of the present invention in Example 19 suppressed the expression of SOD1 mRNA in liver.

---

```
                       SEQUENCE LISTING

<160> NUMBER OF SEQ ID NOS: 6

<210> SEQ ID NO 1
<211> LENGTH: 21
<212> TYPE: DNA
<213> ORGANISM: Artificial sequence
<220> FEATURE:
<223> OTHER INFORMATION: synthesized DNA/RNA; a strand concerning
      Preparation Example 1, wherein 2 nucleotides of 3'-terminus are
      constructed with DNA, and the rest are RNA.

<400> SEQUENCE: 1
gugaugaagu acauccauut t                                              21

<210> SEQ ID NO 2
<211> LENGTH: 21
<212> TYPE: DNA
```

-continued

```
<213> ORGANISM: Artificial sequence
<220> FEATURE:
<223> OTHER INFORMATION: synthesized DNA/RNA; a strand concerning
      Preparation Example 1, wherein 2 nucleotides of 3'-terminus are
      constructed with DNA, and the rest are RNA.

<400> SEQUENCE: 2
aauggaugua cuucaucact t                                                   21

<210> SEQ ID NO 3
<211> LENGTH: 21
<212> TYPE: DNA
<213> ORGANISM: Artificial sequence
<220> FEATURE:
<223> OTHER INFORMATION: synthesized DNA/RNA; a strand concerning
      Preparation Example 1 and 2, wherein 2 nucleotides of 3'-terminus
      are constructed with DNA, and the rest are RNA.

<400> SEQUENCE: 3
gcuaugaaac gauaugggct t                                                   21

<210> SEQ ID NO 4
<211> LENGTH: 21
<212> TYPE: DNA
<213> ORGANISM: Artificial sequence
<220> FEATURE:
<223> OTHER INFORMATION: synthesized DNA/RNA; a strand concerning
      Preparation Example 1 and 2, wherein 2 nucleotides of 3'-terminus
      are constructed with DNA, and the rest are RNA.

<400> SEQUENCE: 4
gcccauaucg uuucauagct t                                                   21

<210> SEQ ID NO 5
<211> LENGTH: 21
<212> TYPE: DNA
<213> ORGANISM: Artificial sequence
<220> FEATURE:
<223> OTHER INFORMATION: synthesized DNA/RNA; a strand concerning
      Preparation Example 1 and 2, wherein 2 nucleotides of 3'-terminus
      are constructed with DNA, and the rest are RNA.

<400> SEQUENCE: 5
gguggaaaug aagaaaguat t                                                   21

<210> SEQ ID NO 6
<211> LENGTH: 21
<212> TYPE: DNA
<213> ORGANISM: Artificial sequence
<220> FEATURE:
<223> OTHER INFORMATION: synthesized DNA/RNA; a strand concerning
      Preparation Example 1 and 2, wherein 2 nucleotides of 3'-terminus
      are constructed with DNA, and the rest are RNA.

<400> SEQUENCE: 6
uacuuucuuc auuccacct t                                                    21
```

The invention claimed is:

1. A polyethylene glycol derivative selected from
   (1) 2-O-(methoxypolyethylene glycol propyl)carbamoyl-1,3-O-dioleoylglycerol, and
   (2) 2-O-(methoxypolyethylene glycol propyl)carbamoyl-1,3-O-distearoylglycerol.

2. A drug carrier comprising a polyethylene glycol derivative according to claim 1 and 2-O-(2-diethylaminoethyl)carbamoyl-1,3-O-dioleoylglycerol.

3. The drug carrier according to claim 2, further comprising a phospholipid.

4. The drug carrier according to claim 2, further comprising cholesterol.

5. A pharmaceutical composition comprising the drug carrier according to claim 2, wherein the pharmaceutical composition includes a pharmaceutical agent.

6. The pharmaceutical composition according to claim 5, wherein the pharmaceutical agent is a single-stranded or double-stranded RNA, a single-stranded or double-stranded DNA, an oligonucleic acid or a water-soluble anionic compound.

7. The pharmaceutical composition according to claim 6, wherein the oligonucleic acid is short interfering RNA, microRNA, short hairpin RNA, antisense DNA, antisense RNA, DNA enzyme, ribozyme, aptamer or non-coding RNA.

8. A method for the therapeutic treatment and/or prophylaxis of inflammatory diseases comprising administering an effective amount of a pharmaceutical composition according to claim 5 to a patient in need thereof.

9. A method for the therapeutic treatment and/or prophylaxis of liver disorders comprising administering an effective amount of a pharmaceutical composition according to claim 5 to a patient in need thereof.

\* \* \* \* \*